(12) United States Patent
Emanuel

(10) Patent No.: US 9,173,976 B2
(45) Date of Patent: Nov. 3, 2015

(54) COMPOSITIONS AND METHODS FOR THE TREATMENT OF BONE VOIDS AND OPEN FRACTURES

(71) Applicant: POLYPID LTD., Petach Tikva (IL)

(72) Inventor: Noam Emanuel, Rehovot (IL)

(73) Assignee: Polypid Ltd., Petach-Tikva (IL)

( * ) Notice: Subject to any disclaimer, the term of this patent is extended or adjusted under 35 U.S.C. 154(b) by 0 days.

(21) Appl. No.: 14/418,138

(22) PCT Filed: Aug. 1, 2013

(86) PCT No.: PCT/IL2013/050657
§ 371 (c)(1),
(2) Date: Jan. 29, 2015

(87) PCT Pub. No.: WO2014/020610
PCT Pub. Date: Feb. 6, 2014

(65) Prior Publication Data
US 2015/0202349 A1 Jul. 23, 2015

Related U.S. Application Data

(60) Provisional application No. 61/678,655, filed on Aug. 2, 2012, provisional application No. 61/739,792, filed on Dec. 20, 2012, provisional application No. 61/778,791, filed on Mar. 13, 2013.

(51) Int. Cl.

| | |
|---|---|
| *A61K 9/00* | (2006.01) |
| *A61K 31/427* | (2006.01) |
| *A61K 31/192* | (2006.01) |
| *A61K 31/65* | (2006.01) |
| *A61P 31/00* | (2006.01) |
| *A61P 31/10* | (2006.01) |
| *A61P 19/08* | (2006.01) |
| *A61P 35/00* | (2006.01) |
| *A61L 27/54* | (2006.01) |
| *A61L 27/12* | (2006.01) |
| *A61L 27/34* | (2006.01) |
| *A61L 27/36* | (2006.01) |

(52) U.S. Cl.
CPC ............ *A61L 27/54* (2013.01); *A61K 31/65* (2013.01); *A61L 27/12* (2013.01); *A61L 27/34* (2013.01); *A61L 27/3608* (2013.01); *A61L 2300/22* (2013.01); *A61L 2300/406* (2013.01); *A61L 2430/02* (2013.01)

(58) Field of Classification Search
None
See application file for complete search history.

(56) References Cited

U.S. PATENT DOCUMENTS

| | | |
|---|---|---|
| 6,793,938 B2 | 9/2004 | Sankaram |
| 2011/0117197 A1* | 5/2011 | Emanuel et al. ............ 424/486 |

FOREIGN PATENT DOCUMENTS

WO    2010/007623 A1    1/2010

OTHER PUBLICATIONS

Emanuel et al., "A Lipid-and polymer-based novel local drug delivery system—BonyPid (TM): from physicochemical aspects to therapy of bacterially infected bones.", J. Controlled Release, 160(2):353-361, Jun. 10, 2012.
Ostermann et al., "Local antibiotic therapy for severe open fractures. A review of 1085 consecutive cases.", J. Bone and Joint Surgery Br., 77(1):93-97, Jan. 1995.
Ho Ayo et al., SA Orthopaedic J., Autumn 2010, pp. 24-29.
International Search Report for PCT/IL2013/050657 published as WO2014020610.
Written Opinion for PCT/IL2013/050657 published as WO2014020610.

* cited by examiner

*Primary Examiner* — Robert A Wax
*Assistant Examiner* — Randeep Singh
(74) *Attorney, Agent, or Firm* — Daniel Feigelson; Fourth Dimension IP

(57) ABSTRACT

The present invention relates to compositions, methods and medical devices for the treatment of bone voids and bone defects. The methods of the invention comprise the step of applying to a bone void or bone defect site a composition comprising a matrix which provides local prolonged release of at least one antibiotic agent at the bone void site.

21 Claims, 8 Drawing Sheets

COMPOSITIONS AND METHODS FOR THE TREATMENT OF BONE VOIDS AND OPEN FRACTURES

This application is a 371 of PCT/IL2013/050657, filed Aug. 1, 2013 and claiming the benefit of provisional applications No. 61/678,655, filed Aug. 2, 2012; 61/739,792, filed Dec. 20, 2012; and 61/778,791, filed Mar. 13, 2013. The contents of these applications are incorporated herein by reference.

FIELD OF THE INVENTION

The present invention relates to compositions, methods and medical devices for the treatment of bone voids or bone defects. Specifically, the method comprises the step of applying to a bone void site a composition comprising a matrix composition which provides local controlled sustained release of at least one antibiotic agent.

BACKGROUND OF THE INVENTION

Bone voids alternatively referred to as bone defects are commonly caused by injury, disease, or surgical interventions. Bone fractures caused mostly by trauma to a bone as well as jaw bone damages caused by trauma, disease or tooth loss are those most commonly associated with bone infections. Early efforts must be made to decontaminate the bones and the surrounding soft tissues and to stabilize the bone void site in order to enable successful bone healing. Unfortunately, the rate and severity of bone infections following such bone void defects is high. Infection is a particularly severe complication of an open fracture and the higher Gustilo types have been shown to have high incidence of this complication. Type-IIIB and type IIIC open fractures have been described as the most critical injuries with as high as 48% of deep bony infections after Type-IIIB fractures. The current oral and intravenous antibiotic treatment allows high concentrations of antibiotics in the blood, but often insufficient local concentration of the drug at the bone voids and specifically in contaminated or infected bone voids defects. Local antibiotic administration is commonly used to overcome poor bone penetration of antibiotic given systemically (intravenously or orally). The first product on the market for local treatment of infected bone is based on antibiotics loaded in poly(methylmethacrylate) (PMMA) bone cement, in the form of antibiotic beads (Osetermann et al., J. Bone and Joint Surgery, 1995, 77B(1):93-97). However, the clinical effect of using this method is hampered by the fact that >90% of the drug remained trapped inside the cement beads. Furthermore, bone cement is not biodegradable and is not osteoconductive, and therefore has to be removed by a second surgical procedure.

Biodegradable polymers such as polylactic/polyglycolide (PLGA), chitosan or collagen were also used as antibiotic-saturated implants in bone lesions. However, such polymeric drug delivery systems cannot maintain a constant and sufficient release rate of antibiotics over the prolonged period of time needed to fully eradicate the invading bacteria. Moreover, the polymeric systems cannot support osteoconductive bone in growth into the void. To overcome these major limitations, antibiotics were added to osteoconductive bone fillers such as calcium sulfate hemihydrate pellets, tricalcium phosphate (TCP) and to calcium hydroxyapatite ceramics. In these bone fillers the release of antibiotics is characterized by a rapid release of the drug in the first week, followed by a sharp decrease in the amounts released after that.

An alternative approach for treating bone infection/bone destruction is using a liposomal drug delivery system to release antibiotics. Liposomes offer a safe and convenient way to control the rate and the location of the delivered drug. But this requires prolonged and repeated systemic applications of the encapsulated drugs in order to achieve complete sterilization of bone and soft tissues. When liposomal antibiotics were combined with osteoconductive elements, most of the drug (~60%) was released in the first 24 h, followed by decreasing amounts in the following days. Thus, the current local delivery systems available do not provide sustainable high local antibiotic concentration at the fracture site during the healing process. Therefore, in spite of the addition of systemic antibiotic treatment with these local treatments, they cannot fully eradicate the bacterial infection in most patients.

Osteoset-T® and PerOssal® are approved biodegradable bone fillers, based on TCP granules, and are used for filling or reconstruction of bone defects in orthopedics, orthodontic and facial surgery. In addition to their osteoconductive properties, these products can also release antibiotics locally, and they are therefore used in infected wounds and in bone defects. Their biodegradability and osteoconductivity suggest a significant advantage over PMMA beads. However, their high burst and the short release period of the drug (antibiotic), for no more than several days following the implantation, represent significant limit to their anti-bacterial effect.

WO 2010/007623 to one of the inventors of the present invention and others provides compositions for extended release of an active ingredient, comprising a lipid-saturated matrix formed from a biodegradable polymer. The present invention also provides methods of producing the matrix compositions and methods for using the matrix compositions to provide controlled release of an active ingredient in the body of a subject in need thereof. These drug delivery matrices provided extended release of the active agent over a period of days, weeks or months.

There is an unmet medical need for effective means for the treatment of bone fractures, and in particular open bone fractures, which promote the bone healing process while preventing infection in a single treatment.

SUMMARY OF THE INVENTION

The present invention relates to compositions, methods and medical devices for the treatment of bone voids or bone defects. The methods of the invention comprise the step of applying to a bone void site a composition comprising a matrix which provides local controlled sustained release of at least one antibiotic agent. In particular embodiments the composition is in the form of a medical device comprising biocompatible bone void fillers coated with a matrix composition which provides local controlled and prolonged release of at least one antibiotic agent at the bone void site. In specific embodiments the composition is in the form of a mixture of uncoated bone void fillers to promote early rapid bone growth at the site of the bone defect and coated bone void fillers to provide antibiotic to the site as well as support bone growth following the degradation of the coating.

The present invention is based in part on unexpected and exceptional clinical data obtained in cases of long bone open fractures types IIIA and IIIB. These types of fractures are known to be associated with a high infection rate in spite of instituting a standard of care (SOC) consisting of early administration of intravenous antibiotics, irrigation and debridement (I&D) and delayed wound closure. Using the compositions and methods of the present invention no infection was observed in any of the treated patients even 6 months post treatment. The fractures were fully united in over 75% of the subjects, after being treated with the medical device of the invention in most cases in a single operative session, without developing any infection at the target fracture, and without developing serious adverse events.

It is now disclosed for the first time, that human subjects with severe long bone open fractures, treated by implanting to the fracture site, during the first surgical intervention after the occurrence of injury, a medical device comprising biocompatible bone void fillers coated with a matrix composition of the present invention which provides local prolonged release of doxycycline, had their bone completely reconstructed without developing any infection at the fracture site even after 6 months. Early signals of callus formation were observed at 8-12 weeks post implantation in all treated subjects. Exceptionally, infection free recovery was achieved even when an open fracture was first treated and implanted with the medical device more than 5 days post trauma (i.e. highly contaminated wound characterized by the presence of bacterial biofilm). According to one aspect, the present invention provides a matrix composition which provides local controlled release of an antibiotic agent at the location at which bone growth is desired, optionally in the form of a medical device comprising biocompatible bone void fillers coated with the matrix composition which provides local controlled release of an antibiotic agent at the location at which bone growth is desired.

According to some embodiments, the biodegradable matrix composition comprises: (a) a biodegradable polyester selected from PLA, PGA and PLGA; (b) cholesterol; (c) a combination of phosphatidylcholines having fatty acid moieties of 16-18 carbons; and (e) an antibiotic agent. In specific embodiments, the polymer and the phospholipids form a structurally ordered lipid saturated matrix composition that is substantially free of water. In some embodiments, the matrix composition is has a highly organized multilayer structure in which the polymer and lipids are organized in the form of multiple alternating layers. In some embodiments, the biodegradable, slow release coating formulation (matrix) comprises at least 50% total lipids by weight. In some embodiments, the biodegradable, slow release coating formulation (matrix) comprises at least 40% phospholipids by weight. In some embodiments, the biodegradable, slow release coating formulation comprises at least 10% polymer by weight. In some embodiments, the biodegradable, slow release coating formulation (matrix) comprises at least 5% antibiotic by weight.

According to some embodiments, the matrix composition of the present invention comprises a continuous structure devoid of internal gaps and/or free volume. According to some embodiments, the matrix composition is lipid saturated indicating that the space between the polymer layers or polymer backbone is filled with lipid molecules in combination the antibiotic agent, to the extent that additional lipid moieties can no longer be incorporated into the matrix to an appreciable extent.

In some embodiments, the matrix composition is capable of releasing at least 50% of the antibiotic agent at zero-order kinetics. In some embodiments, at least 60% of the antibiotic agent is released from the matrix composition at zero-order kinetics. Without being limited by a specific theory or mechanism of action it is suggested that this organized structure or substructure of the matrix composition of the invention is one of the main reasons for the zero-order release rate of the drug or drugs from the matrix formulation following its hydration. Thus, the zero order release rate may be attributed to slow and continuous "peeling" of drug together with the formulation components from the hydrated surface layer(s) of the highly organized layers of lipids and polymer. According to some embodiments the matrix of the present invention is water resistant. As such water cannot easily, if at all, diffuse into the matrix and the pharmaceutically active agent entrapped between the layers cannot easily, if at all, diffuse out of the matrix. According to some embodiments, the drug is being released from the matrix compositions of the present invention upon the gradual surface degradation of the matrix, thus enabling extended release on a scale of 3-5 weeks, wherein the majority (at least 50%) of the antibiotic active agent is being released with zero order kinetics.

According to some embodiments the biodegradable matrix comprises (a) PLGA; (b) cholesterol; (c) DPPC; (d) DSPC and (e) an antibiotic agent.

According to some embodiments, the matrix composition comprises about 1-20% (w/w) of the antibiotic agent. According to some embodiments, the matrix composition comprises about 5-15% (w/w) of an antibiotic agent. According to certain typical embodiments, the matrix composition comprises about 8-12% (w/w) of the antibiotic agent. According to certain typical embodiments, the matrix composition comprises about 10% (w/w) antibiotic agent.

According to some embodiments the biodegradable matrix composition comprises a tetracycline antibiotic agent. According to some embodiments, the matrix composition comprises Doxycycline (e.g. doxycycline hyclate), an antibiotic from the tetracycline family of antibacterial drugs. According to some embodiments, the matrix composition comprises about 1-20% (w/w) Doxycycline. According to some embodiments, the matrix composition comprises about 5-15% (w/w) Doxycycline. According to certain typical embodiments, the matrix composition comprises about 8-12% (w/w) Doxycycline.

According to certain typical embodiments, the matrix composition comprises about 10% (w/w) Doxycycline.

According to some embodiments, the matrix composition comprises about 10-30% (w/w) PLGA. According to some embodiments, the matrix composition comprises about 15-25% (w/w) of PLGA. According to certain typical embodiments, the matrix composition comprises about 20% (w/w) of PLGA.

According to some embodiments, the matrix composition comprises about 5-20% (w/w) of cholesterol. According to some embodiments, the matrix composition comprises about 5-15% (w/w) of cholesterol. According to some embodiments, the matrix composition comprises about 7-13% (w/w) of cholesterol. According to some embodiments, the matrix composition comprises about 9-11% (w/w) of cholesterol. According to certain typical embodiments, the matrix composition comprises about 10% (w/w) of cholesterol.

According to some embodiments, the matrix composition comprises at least about 40% (w/w) of one or more phosphatidylcholine molecules having fatty acid moieties of at least 14 carbons. According to some embodiments, the matrix composition comprises at least about 50% (w/w) of one or more phosphatidylcholine molecules having fatty acid moieties of at least 14 carbons. According to some embodiments, the matrix composition comprises about 40-75% (w/w) of one or more phosphatidylcholine molecules having fatty acid moieties of at least 14 carbons. According to some embodiments, the matrix composition comprises about 50-70% (w/w) of one or more phosphatidylcholine molecules having fatty acid moieties of at least 14 carbons. According to certain typical embodiments, the matrix composition comprises about 60% (w/w) of one or more phosphatidylcholine molecules having fatty acid moieties of at least 14 carbons. According to some embodiments, the phosphatidylcholine molecules of the composition comprise DPPC. According to some embodiments, the phosphatidylcholine molecules of the composition comprise DSPC. According to some embodiments, the matrix composition comprises a mixture of DPPC and DSPC. Typically the ratio between DPPC and DSPC in the formulation is between about 10:1 to 1:1; preferably between 5:1 and 2:1; more preferably the ratio between DPPC and DSPC in the formulation is about 3:1. According to some embodiments, the matrix composition comprises about 50-70% (w/w) of a mixture of DPPC and DSPC wherein the ratio of DPPC and DSPC is about 3:1.

According to some embodiments, the matrix composition comprises about 15-25% (w/w) of PLGA, about 5-15% (w/w) of cholesterol, about 50-70% (w/w) of a mixture of DPPC and DSPC wherein the ratio of DPPC and DSPC is between about 5:1 and 2:1 and about 7-12% (w/w) of Doxycycline. According to some embodiments, the matrix composition comprises about 20% (w/w) of PLGA, about 10% (w/w) of cholesterol, about 60% (w/w) of a mixture of DPPC and DSPC wherein the ratio of DPPC and DSPC is 3:1 and about 10% (w/w) of Doxycycline.

In some embodiments the biodegradable matrix composition is incorporated into a medical device comprising biocompatible bone void fillers coated with a matrix composition which provides local controlled and prolonged release of at least one antibiotic agent at the bone void site. According to some embodiments, the bone void filler is selected from allogeneic (i.e., from human sources), xenogeneic (i.e., from animal sources), synthetic bone void fillers or any combination thereof. According to some embodiments, the bone void filler is synthetic. According to some embodiments, the synthetic bone void filler is composed of Tri-Calcium Phosphate (β-TCP). According to some embodiments, the bone void filler is in the form of a powder having an average particle (or granule) size of 3.0 mm or less, alternatively having an average size of less than 2 mm, alternatively having an average size of less than 1.5 mm; alternatively, having an average size of less than 1.0 mm, alternatively having an average size of 0.1-0.5 mm. According to certain typical embodiments, the bone filler is β-TCP having an average particle size of 0.5-1.0 mm.

Without wishing to be bound by theory or mechanism of action, following its implantation, the coated bone filler particles release the antibiotic drug into the bone void and its surroundings over a pre-set, prolonged, controlled period of time. The bone filler scaffold supports osteoconductive bone recovery, while the controlled, prolonged release of the antibiotic drug formulation coating successfully eradicates or prevents bone infection. The antibacterial activity of the released antibiotic is ancillary to the osteoconductive activity of the bone filler, and prevents its potential rejection or early absorption by bacteria related local bone infection.

According to some embodiments, the coated particles of the invention comprise between about 80-90% (w/w) of bone void filler and 10-20% (w/w) of the matrix composition as described above. According to some embodiments, the coated particles of the invention comprise between about 85-90% (w/w) of bone void filler and 10-15% (w/w) of the matrix composition. According to certain typical embodiments the coated particles comprise 80-90% (w/w) of β-TCP, preferably β-TCP having an average particle size of 1.0 mm or less. According to some specific embodiments, the medical device comprises coated particles wherein the coated particles contain about 88% (w/w) of β-TCP having an average particle size of 0.5-1.0 mm coated with a matrix composition consisting essentially of about 2.4% PLGA, about 1.2% cholesterol, about 5.5% of DPPC, about 1.8% DSPC and about 1.2% of doxycycline hyclate.

According to some embodiments, the medical device of the invention may further comprise any commercially available non-coated bone void fillers (e.g. allogeneic, xenogeneic or synthetic). The non-coated bone filler mixed with the coated particles of the invention may be the same as the coated bone filler particles. For example, the coated and the non-coated bone void fillers may be both composed of β-TCP. Alternatively, the non-coated bone filler, may be different from the coated bone filler. Alternatively, the medical device of the invention may comprise a mixture of non-coated bone void particles in addition to the coated particles. According to some embodiments, the medical device of the invention may be mixed with autograft bone material prior to its implantation at the bone void. According to some embodiments the weight of non-coated particles in the medical device of the invention is lower than 75% (w/w) of the total weight of the medical device. According to some embodiments, the weight of the non-coated particles in the medical device of the invention is lower than 70% (w/w) of the total weight of the medical device. According to some embodiments, the weight of the non-coated particles in the medical device of the invention is lower than 60% (w/w) of the total weight of the medical device. According to some embodiments, the weight of the non-coated particles in the medical device of the invention is about 50% (w/w) of the total weight of the medical device, or lower. According to some embodiments, the weight ratio of the coated to non-coated bone filler is between 1:3 and 10:1. According to some embodiments, the weight ratio of the coated to non-coated bone filler is between 1:3 and 5:1. Alternatively between 1:2 and 2:1. Alternatively, the weight ratio of the coated to non-coated bone filler is 1:1.

According to some embodiments, the medical device comprises a combination of coated and non coated β-TCP having an average particle size of 0.1-1 mm in a ratio of 1:1. According to some specific embodiments, the medical device comprises a combination of coated and non coated β-TCP having an average particle size of 0.5-1.0 mm in a ratio of 1:1. According to additional specific embodiments, the medical device comprises a combination of coated and non coated β-TCP having an average particle size of 0.1-0.5 mm in a ratio of 1:1.

According to some embodiments, the medical device comprises a combination of coated and non-coated β-TCP at a ratio of 1:1, wherein the total weight ratio between the medical device ingredients is 90-95% (w/w) of β-TCP, 1.0-2.0% PLGA, about 0.4-0.8% cholesterol, about 2.0-4.0% of DPPC, about 0.7-1.3% DSPC and about 0.4-2% of doxycycline. According to certain embodiments, the medical device comprises a combination of coated and non-coated β-TCP at a ratio of 1:1, wherein the total weight ratio between the medical device ingredients is 93-94% (w/w) of β-TCP, 1.1-1.5% PLGA, about 0.6-0.7% cholesterol, about 2.7-3.2% of DPPC, about 0.9-1.1% DSPC and about 0.6-0.7% of doxycycline hyclate. According to certain specific embodiments, the medical device comprises a combination of coated and non-coated β-TCP at a ratio of 1:1, wherein the total weight ratio between the medical device ingredients is 93.5% (w/w) of β-TCP, 1.3% PLGA, about 0.63% cholesterol, about 2.94% of DPPC, about 0.98% DSPC and about 0.65% of doxycycline hyclate. According to some embodiments, the β-TCP particles have an average particle size of 500-1000 μm.

According to some embodiments, every 10 grams of the medical device according to the present invention comprises between about 0.4 and about 2.0 g of the Doxycycline.

According to some embodiments, every 10 grams of the medical device according to the present invention comprises between about 0.4 and about 1.0 g of Doxycycline. According to further embodiments, every 10 grams of medical device according to the present invention comprises between about 0.5 and about 0.8 g of Doxycycline. According to certain preferred embodiments, every 10 grams of medical device according to the present invention comprises about 65 mg of Doxycycline.

According to another aspect of the present invention the medical device is used for implantation at a location at which bone growth is desired.

According to another aspect, the present invention provides methods for treating a patient comprising implanting at a location at which bone growth is desired a matrix composition which provides local controlled release of an antibiotic agent at the location at which bone growth is desired, optionally in the form of a medical device comprising biocompatible bone void fillers coated with the matrix composition which provides local controlled release of an antibiotic agent at the location at which bone growth is desired.

According to some embodiments, the present invention provides a method for the treatment of bone fractures, the method comprising the steps of applying to a fracture site a medical device comprising biocompatible bone void fillers coated with a matrix composition which provides local controlled release of an antibiotic agent at the fracture site.

According to some embodiments, the location at which bone growth is desired is a bone void. The bone void may be for example a result of injury (e.g. bone fractures), removal of bone pathology (e.g. at surgical procedures), a tooth extraction, or any other case resulting with significant loss of skeletal structure. According to some embodiments, the location at which bone growth is desired is a bone fracture. According to some embodiments, the location at which bone growth is desired is a bone open fracture. According to some embodiments, the location at which bone growth is desired is a long bone open fracture.

According to some embodiments, the methods of the invention are useful in cases where the bone void site is sterile, contaminated or even infected at the time of implantation.

According to some embodiments, the implanted medical device is shaped to conform to the bone void in a patient.

According to some embodiments, the present invention provides methods for the treatment of bone fractures in a subject, the method comprising the step of applying to a fracture site a medical device comprising biocompatible bone void fillers coated with a matrix composition which provides local controlled release of an antibiotic agent at the fracture site.

According to some embodiments, the methods of the invention are useful for the treatment of open contaminated/infected fractures. According to certain typical embodiments, the methods of the invention are useful for the treatment of open long bone fractures. According to currently preferred embodiments, the methods of the invention are useful for the treatment of open long bone Gustilo fractures grade II, grade IIIa, IIIb and grade IIIc.

According to some embodiments, the methods of the present invention are suitable for the treatment of bone fractures in a human subject. According to some embodiments, the methods of the present invention are suitable for the treatment of bone fractures in men and women. According to some embodiments, the methods of the present invention are suitable for the treatment of bone fractures in infants, children, and adolescents.

According to some embodiments, the medical device of the invention is administered at a dose ranging from 1-40 grams per one bone fracture site. According to certain embodiments, the medical device of the invention is administered at a dose ranging from 5-20 grams per one bone fracture site. It is to be understood that depending on the status of the fracture a higher or a lower dose can be used per one bone fracture at the discretion of the skilled in the art. Following the insertion, or implantation of the medical device of the invention into a bone fracture site, the coated bone void fillers release the drug into the bone void and the surrounding over a predetermined, prolonged, controlled period of time. The bone filler scaffold supports osteoconductive bone recovery, by re-absorbing and being replaced by bone during the healing process. In addition, its osteoconductive properties will enhance callus formation and bone healing, while the controlled, prolonged release of the anti-bacterial drug from the coating formulation successfully eradicates or prevents bone infection. The anti-bacterial activity of the released antibiotic is ancillary to the osteoconductive activity of the bone void fillers, and prevents its potential rejection or early absorption by bacteria related to local bone infection, and prevent the development of acute or chronic bone infections following contamination.

According to some embodiments, the methods of the present invention are useful for the treatment and prevention of bone infections in general.

The medical device according to the invention is administrated locally or topically.

The medical device according to some embodiments of the invention may be used in applications where bone fillers which do not contain antibiotics are contraindicated.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
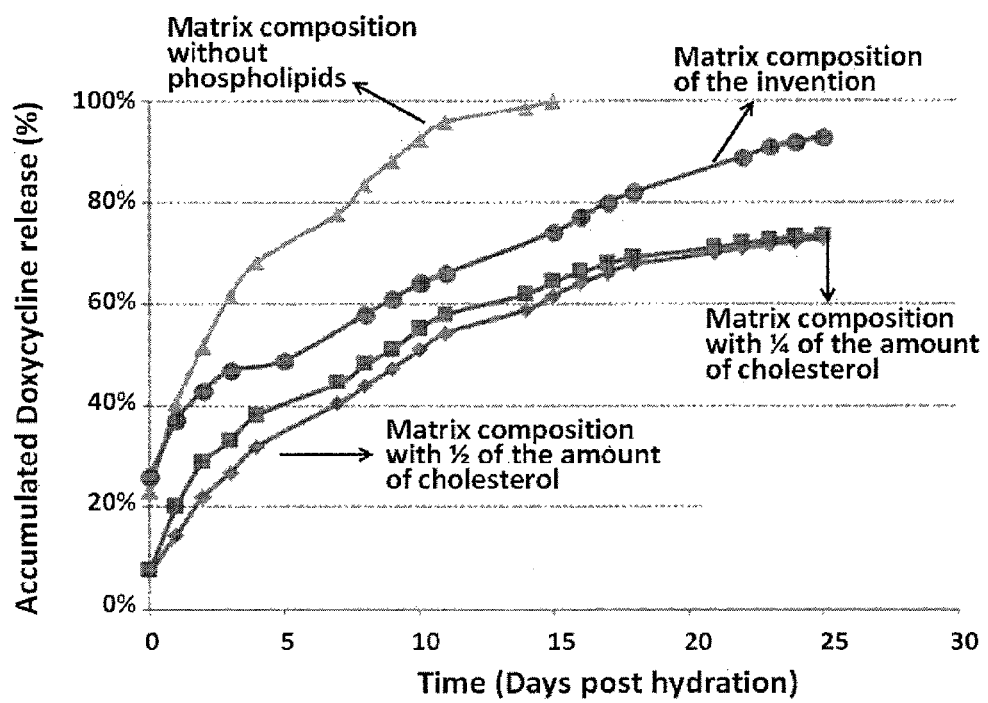
FIG. 1 shows the accumulated release profile of doxycycline from hydrated bone particles coated with the matrix composition of the invention (comprising about 10% (w/w) of cholesterol and about 60% (w/w) of phospholipids) vs. the release from bone particles coated with compositions comprising smaller amounts of cholesterol or lacking phospholipids.

The present invention relates to compositions, methods and medical devices for the treatment of bone voids or bone defects. The methods of the invention comprise the step of applying to a bone void site a composition comprising a matrix which provides local controlled release of at least one antibiotic agent. In particular embodiments the composition is in the form of a medical device comprising biocompatible bone void fillers coated with a matrix composition which provides local controlled and prolonged release of at least one antibiotic agent at the bone void site. In specific embodiments the composition is in the form of a mixture of uncoated bone void fillers to promote bone growth at the site of the bone defect and coated bone void fillers to provide antibiotic to the site.

As used herein "bone void" alternatively referred to as "bone defect" refers to any bone deficient region, such as a void, gap, recess, or other discontinuity in the bone. The bone defect can be artificially or naturally established, and can occur due to disease or trauma. Thus, the bone defect can occur as a consequence of pathologic, inflammatory, or tumor diseases, surgical interventions, congenital defects, or bone fractures, and the like. For example, in the case of certain diseases, such as bone tumors, the bone defect is artificially established by removing the tumor tissue. Thus, according to the method of the subject invention, the medical device can be applied, for example, to repair periodontal defects, for craniofacial reconstruction, joint reconstruction, and fracture repair, to conduct for example orthopedic surgical procedures.

As used herein, "treatment of bone voids or bone defects" relates to bone healing by filling and/or covering a bone void and promoting bone growth at the bone void or bone defected site.

General Characteristics of the Matrix Compositions of the Invention.

According to some embodiments, the biodegradable matrix composition comprises: (a) a biodegradable polyester selected from PLA, PGA and PLGA; (b) cholesterol; (c) a combination of phosphatidylcholines having fatty acid moieties of 16-18 carbons; and (e) an antibiotic agent. In specific embodiments, the polymer and the phospholipids form a structurally ordered lipid saturated matrix composition that is substantially free of water. In some embodiments, the matrix composition is has a highly organized multilayer structure in which the polymer and lipids are organized in the form of multiple alternating layers. In some embodiments, the biodegradable, slow release coating formulation comprises at least about 50% total lipids by weight. In some embodiments, the biodegradable, slow release coating formulation comprises at least about 40% phospholipids by weight. In some embodiments, the biodegradable, slow release coating formulation comprises between about 40-75% phospholipids by weight. In some embodiments, the biodegradable, slow release coating formulation comprises between about 50-70% phospholipids by weight. In some embodiments, the biodegradable, slow release coating formulation comprises between about 55-65% phospholipids by weight. In some embodiments, the biodegradable, matrix composition comprises at least 10% polymer by weight. In some embodiments, the biodegradable, matrix composition comprises between about 10-30% polymer by weight. In some embodiments, the biodegradable, matrix composition comprises between about 15-25% polymer by weight. In some embodiments, the biodegradable, slow release coating formulation comprises at least about 5% antibiotic by weight.

The biodegradable polyester used in the matrix compositions of the present invention may be selected from the group consisting of PLA (polylactic acid). "PLA" refers to poly(L-lactide), poly(D-lactide), and poly(DL-lactide). In another embodiment, the polymer is PGA (polyglycolic acid). In another embodiment, the polymer is PLGA (poly(lactic-co-glycolic acid). The PLA contained in the PLGA may be any PLA known in the art, e.g. either enantiomer or a racemic mixture.

The PLGA of methods and compositions of the present invention has, in another embodiment, a 50:50 lactic acid/glycolic acid ratio. In another embodiment, the ratio is 60:40. In another embodiment, the ratio is 75:25. In another embodiment, the ratio is 85:15. In another embodiment, the ratio is 90:10. In another embodiment, the ratio is 95:5. In another embodiment, the ratio is another ratio appropriate for an extended in vivo release profile. The PLGA may be either a random or block copolymer. Each possibility represents a separate embodiment of the present invention. It is to be emphasized that the polymer may be of any size or length (i.e of any molecular weight).

The matrix compositions of the present invention are lipid saturated. "Lipid saturated," as used herein, refers to saturation of the polymer of the matrix composition with cholesterol and phospholipids in combination with any hydrophobic drug present in the matrix, and any other lipids that may be present. The matrix composition is saturated by whatever lipids are present. In another embodiment, "lipid saturation" refers to filling of internal gaps (free volume) within the lipid matrix as defined by the external border of the polymeric backbone. The gaps are filled with phosphatidylcholines in combination with cholesterol and possibly other type of lipids and antibiotic agent present in the matrix, to the extent that additional lipid moieties can no longer be incorporated into the matrix to an appreciable extent.

In another embodiment, the matrix composition of the present invention is substantially free of water. "Substantially free of water" refers, in another embodiment, to a composition containing less than 1% water by weight. In another embodiment, the term refers to a composition containing less than 0.8% water by weight. In another embodiment, the term refers to a composition containing less than 0.6% water by weight. In another embodiment, the term refers to a composition containing less than 0.4% water by weight. In another embodiment, the term refers to a composition containing less than 0.2% water by weight. In another embodiment, the term refers to the absence of amounts of water that affect the water-resistant properties of the composition. In another embodiment, the term refers to a composition manufactured without the use of any aqueous solvents. In another embodiment, producing the composition using a process substantially free of water enables lipid saturation. Lipid saturation confers upon the matrix composition ability to resist bulk degradation in vivo; thus, the matrix composition exhibits the ability to mediate extended release on a scale of several weeks or months. Each possibility represents a separate embodiment of the present invention.

In another embodiment, the matrix composition is essentially free of water. "Essentially free" refers to a composition comprising less than 0.1% water by weight. In another embodiment, the term refers to a composition comprising less than 0.08% water by weight. In another embodiment, the term refers to a composition comprising less than 0.06% water by weight. In another embodiment, the term refers to a composition comprising less than 0.04% water by weight. In another embodiment, the term refers to a composition comprising less than 0.02% water by weight. In another embodiment, the term refers to a composition comprising less than 0.01% water by weight. Each possibility represents a separate embodiment of the present invention.

In another embodiment, the matrix composition is free of water. In another embodiment, the term refers to a composition not containing detectable amounts of water. Each possibility represents a separate embodiment of the present invention.

In another embodiment, the matrix composition is dry. "Dry" refers, in another embodiment, to the absence of detectable amounts of water or organic solvent.

In another embodiment, the water permeability of the matrix composition has been minimized. "Minimizing" the water permeability refers to a process of producing the matrix composition in organic solvents, in the presence of an the amount of lipid that has been determined to minimize the permeability to penetration of added water.

The term "about" with reference to weight percentages, particle sizes and weight ratios refers to a particular variable and a range around that variable that is within about 10% of the value of the variable.

Technology Platform of the Medical Device of the Invention

The efficacy of a drug is commonly determined by its local concentration. That, in turn, is determined by the ratio between the accumulation rate of drug released from the product vs. its elimination by physical distribution to surrounding tissue, as well as by neutralization and/or degradation. An optimal drug delivery system should release the drug according to the biological need, in order to create an effective concentration at close proximity to the target and throughout a sufficient period of time needed for the desired biological effect. This can be achieved by releasing the active form of the drug near the target at a rate that will result in an effective concentration that is above the minimal effective rate, but below the toxic level and for the desired period of time needed for effective therapeutic effect.

One of the ways to gain better control over local exposure of a given drug is by controlling its supply rate. The supply rate is dictated by 1) the drug release profile, 2) the release rate and 3) the duration of release. These parameters are closely related; while the release rate is strongly depended on the specific formulation, the duration is a function of two factors: release rate and the size of drug reservoir.

The biodegradable matrix composition of the invention comprising a combination of specific lipids and polymers loaded with an antibiotic agent determines not only the release rate profile of the drug, but also allows control over the release rate during a prolonged zero-order kinetic stage. It has been found that antibiotic release duration of 3-4 weeks, resulting with a local concentration of at least 5 times the MIC (Minimum inhibitory concentration) of the antibiotic agent against the bacteria (e.g. S. aureus) is an optimal duration to fully eradicate local infection. Additionally, initial release of antibiotic at the contaminated site, such as a contaminated open fracture, is very important since the initial antibacterial immune attacked may be compromised in situations involving hematoma. Therefore, the most effective profile will combine initial release, resulting with an effective local concentration of antibiotic, followed by continuous, zero order kinetics, release over sufficient duration, preferably at least 3-4 weeks. The initial release should be limited so as to leave sufficient reservoir to support subsequent prolong release. It has been found that the matrix composition of the present invention comprising about 15-25% (w/w) of PLGA, about 5-15% (w/w) of cholesterol, about 50-70% (w/w) of a mixture of DPPC and DSPC wherein the ratio of DPPC and DSPC is between about 5:1 and 2:1 and about 7-12% (w/w) of Doxycycline, displays initial release of up to about 35% of the entrapped antibiotic and preferably up to 30% of the entrapped antibiotic. The amount of drug released immediately post hydration is clinically safe, and leaves most of the drug (at least 65%) to the prolong delivery for about 3-5 weeks, and can elevate local concentration to 10-50 MIC or more.

The currently available products used for local release of antibacterial agents into contaminated or infected bone voids typically utilize polymers (commonly in the form of vesicles). Whereas a polymer-based drug delivery system features a long lasting release, it also has the drawback of an initial high burst release. On the other hand, while a liposome-based drug delivery system features a low burst release, it has the drawback of a short lasting release.

The optimization of the release rate is essential for effective treatment. The release rate can compensate to the loss of active drug due to clearance with body fluids (plasma and lymph), uptake by cells and bacteria, degradation via enzymes and chemical degradation due to pH and/or hydration, neutralization by bone surfaces, proteins and more. The determination of the release rate need also to take into consideration the space volume to where the antibiotic drug is released, should also be considered when determining the desired release rate.

In a medical device of the invention, the space volume is determined by the free space within and between the bone filler granules. Typically bacteria can penetrate into such free space. The space volume is related to the volume of the composition implanted. Therefore, the optimal release rate is mainly determined by the intrinsic characteristics of the product itself.

The medical device of the present invention gradually releases the anti-biotic agent at a constant release rate (zero order kinetics), resulting with a local concentration of the drug within the bone filler particles that is at least 10 times the MIC of the antibiotic against S. aureus bacteria (typically about 0.1-0.5 µg/ml) over 3-4 weeks. S. aureus is the most common bone contaminating bacteria.

The medical device of the present invention enables to entrap a large variety of one or more biologically active molecules and to release them at a pre-programmed rate for periods ranging from several weeks to several months.

This biocompatible and biodegradable family of drug carriers supplies implantable solutions for complicated medical conditions, such as open bone fractures.

The medical device of the invention is indicated according to some embodiments as bone void filler in open contaminated/infected fractures. It is composed of biodegradable bone void fillers (ceramic bone graft) that supports bone growth by its osteoconductive properties which is microcoated by a biocompatible and biodegradable formulation comprising a lipid saturated matrix comprising a biodegradable polymer and an antibacterial drug (e.g. Doxycycline). The coating gradually releases the anti-bacterial agent into the surrounding tissues during about 30 days from its implantation. The bone filler is resorbed and replaced by bone during the healing process and the antibiotic eradicates or reduces bone infection and allows for successful bone healing.

The medical device of the invention releases the antibiotics locally at a predictable, long-term rate. Thus, the therapeutic antibiotic levels can be maintained locally at the graft site, while maintaining low or no systemic levels.

The medical device of the invention, thus advantageously combines between the antibacterial activity of the released antibiotic and the osteoconductive activity of the bone void filler, and prevents its potential rejection or early absorption by bacteria related local bone infection. The therapeutic antibiotic levels are maintained locally at the graft site, while maintaining low or no systemic plasma levels.

Due to the prolonged release of the local antibiotic, for up to 30 days, a small and safe dose of local antibiotic, which is equal to a single dose commonly administered I.V., is highly effective in eradicating local bacterial infections in open fractures. By way of example, the amount of antibiotic in 10 grams of the medical device of the invention is about the same as the amount of antibiotic in a single dose commonly administered I.V. or a single pill (or tablet) for oral use.

Due to the bioresorbable and biocompatible properties of the medical device of the invention, no additional surgery is required for removal of the device (in contrast to other products, such as PMMA). Implantation of the medical device of the invention at the fracture site (e.g. open fracture site) promotes the bone healing process while preventing infection in a single treatment. Thus, by using the medical device of the invention the hospitalization time post-surgical procedure significantly decreases, as well as the need for costly and potentially toxic IV antibiotics for lengthy course.

The medical device of the invention is comprised of well-known and approved components for medical use.

The medical device of the invention comprises biocompatible bone void fillers coated with a biodegradable matrix composition which provides local controlled release of an antibiotic agent at the fracture site. According to some embodiments, the bone void filler particles are coated with the biodegradable matrix composition, wherein the coatings are of a thickness of 200 µm or less; preferably the coatings are of a thickness of 100 µm or less; preferably the coatings are of a thickness of 80 µm or less; preferably the coatings are of a thickness of 70 µm or less; preferably the coatings are of a thickness of 60 µm or less; preferably the coatings are of a thickness of 50 µm or less; preferably the coatings are of a thickness of 40 µm or less; preferably the coatings are of a thickness of 30 µm or less; preferably the coatings are of a thickness of 20 µm or less.

In treatment of bone fractures, open bone fractures in particular, as well as other orthopedic surgery one of the greatest risks is infection. Antibiotics that are commonly used to treat patients undergoing orthopedic surgery are aminoglycoside antibiotic such as gentamicin or tobramycin. The use of the tetracycline family of drugs in general, and doxycycline in particular in orthopedic procedures is not common.

Doxycycline is a member of the tetracycline antibiotics group, and is commonly used to treat a variety of infections. Doxycycline is a semisynthetic tetracycline, synthetically derived from oxytetracycline.

Doxycycline can be effectively used for treating infections caused by many types of both Gram-negative and Gram-positive bacteria and is used for treating a number of conditions. Most importantly, Doxycycline is highly effective against Staphylococcus aureus (S. aureus), the most common bacteria related to bone infections. Furthermore, bacteriologic testing indicates appropriate susceptibility to the drug by Methicillin-resistant Staphylococcus aureus (MRSA), a bacterium responsible for several difficult-to-treat infections in humans (named also as multidrug-resistant Staphylococcus aureus and oxacillin-resistant Staphylococcus aureus (ORSA)).

The minimal inhibitory concentrations (MIC) of Doxycycline against common bacteria, as well as such S. aureus are relatively low, and can be as low as 0.1 µg/ml (for S. aureus), allowing high potency in vivo against common bone contaminations. The tetracycline family, including Doxycycline, inhibits cell growth by inhibiting translation. It binds to the 16S part of the 30S ribosomal subunit and prevents the aminoacyl tRNA from binding to the A site of the ribosome. The binding is reversible in nature. As with other tetracyclines, bacteria may become resistant to Doxycycline by different mechanisms: enzymatic inactivation of tetracycline, efflux, and ribosomal protection. However, resistance to Doxycycline is much less frequent than to penicillin antibiotics, as was demonstrated for S. aureus, where only about 10% of the isolated sub species in the clinic were resistant to Doxycycline vs. more than 50% to penicillin, and about 30-40% to gentamicin (Shaarei-Zedek Jerusalem Medical Center Database).

Doxycycline is approved for treating bone related infections in the marketed drug delivery product ATRIDOX®. This product, is indicated for use as a subgingival controlled-release product, composed of ATRIGEL® Delivery System, which is a bioabsorbable, polymeric formulation composed of 36.7% poly (DL lactide) (PLA). The constituted product has a concentration of 10% of Doxycycline. Upon contact with the crevicular fluid, the liquid product solidifies and then allows for controlled release of drug for a period of 7 days.

Thus, Doxycycline is an effective and highly potent broad spectrum antibiotic. Its high potency and the relatively rare resistance to Doxycycline by S. aureus are highly beneficial in treating or preventing bone infections. The overall safety profile of Doxycycline, as well as the experience in treating bone related infections in the clinic, justifies the use of this potent antibiotic as the first choice in the medical device of the invention.

According to some embodiments, the antibiotic agent of methods and compositions of the present invention is, in one embodiment, doxycycline. In another embodiment, the antibiotic is a hydrophobic tetracycline. Non-limiting examples of hydrophobic tetracyclines are 6-demethyl-6-deoxytetracycline, 6-methylene tetracycline, minocycline (also known as 7-dimethylamino-6-demethyl-6-deoxytetracycline), and 13-phenylmercapto-a-6-deoxy-tetracycline. In another embodiment, the antibiotic is selected from the group consisting of doxycycline, tetracycline, and minocycline. In another embodiment, the antibiotic is integrated into the matrix composition. In another embodiment, at least one antibiotic is integrated into the matrix composition. In another embodiment, a combination of antibiotic drugs is integrated into the matrix composition.

In alternative embodiments, the antibiotic is selected from the group consisting of amoxicillin, amoxicillin/clavulanic acid, penicillin, metronidazole, clindamycine, chlortetracycline, demeclocycline, oxytetracycline, amikacin, gentamicin, kanamycin, neomycin, netilmicin, streptomycin, tobramycin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, chloramphenicol, clofazimine, colistimethate, colistin, cycloserine, fosfomycin, furazolidone, methenamine, nitrofurantoin, pentamidine, rifabutin, rifampin, spectinomycin, trimethoprim, trimetrexate glucuronate, and vancomycin. In another embodiment, the biologically active ingredient is an antiseptic drug such as chlorhexidine. Each antibiotic represents a separate embodiment of the present invention. According to some embodiments, the medical device of the invention comprises biocompatible bone void fillers coated with a matrix composition which provides local controlled prolonged release of an antibiotic agent or a combination of antibiotic agents at the fracture site.

Bone Grafting:

Bone grafting is a surgical procedure that replaces missing bone in order to repair bone fractures that are extremely complex, pose a significant health risk to the patient, or fail to heal properly. Bone generally has the ability to regenerate completely, but requires a very small fracture space or some sort of scaffold to do so. In 1998, slightly more than 300,000 bone graft procedures were performed in the United States. Currently, this figure exceeds 500,000 in the US and approximately 2.2 million worldwide. The estimated cost of these procedures approaches $2.5 billion per year.

Approximately 60% of the bone graft substitutes currently available involve ceramics, either alone or in combination with another material. These include calcium sulfate, bioactive glass, and calcium phosphate.

Synthetic bone void fillers, such as tri calcium phosphate TCP, are available for a variety of indications in orthopedic surgery. Use of synthetic bone void fillers poses much less risk of infection and rejection of the graft, since its mechanical properties are comparable to bone.

The antibacterial activity of the released antibiotic is ancillary to the osteoconductive activity of the bone void filler particles, and prevents their potential rejection or early absorption by bacteria related local bone infection.

The medical device of the invention, because of its resorbable coated bone graft substitute, may release antibiotics locally at a predictable, long-term rate. The therapeutic antibiotic levels can be maintained locally at the graft site, while maintaining low and non-toxic systemic levels of the antibiotic agent.

Preclinical, Toxicology and Biocompatibility Studies

The medical device of the invention has been tested in vivo in infected rabbits' tibia model. The medical device of the invention has demonstrated its high effectiveness both in acute and in chronic infections, and was shown to be significantly advantageous over the non-formulated free drug and multiple administration of systemic antibiotics. The medical device of the invention is safe for use as assessed during clinical trials. Particularly, no differences in hematology and/or blood chemistry parameters were observed upon treatment with the medical device of the invention; no systemic adverse effects were attributed by implantation of the medical device of the invention.

Gustilo Open Fracture Classification

The methods of the invention are useful for the treatment of open contaminated/infected fractures. According to certain typical embodiments, the methods of the invention are useful for the treatment of open long bone fractures. According to currently preferred embodiments, the methods of the invention are useful for the treatment of open long bone classified as Gustilo fractures grade II, grade IIIa and grade IIIb.

Gustilo open fracture classification is the most commonly used classification system for open fractures. This system uses the amount of energy, the extent of soft-tissue injury and the extent of contamination for determination of fracture severity. Progression from grade I to IIIC implies a higher degree of energy involved in the injury, higher soft tissue and bone damage and higher potential for complications. Important to recognize that grade IIIC fracture implies vascular injury as well.

Type I: Open fracture, clean wound, wound <1 cm in length.

Type II: Open fracture, wound >1 cm in length without extensive soft-tissue damage, flaps, avulsions.

Type III: Open fracture with extensive soft-tissue laceration, damage, or loss or an open segmental fracture. This type also includes open fractures caused by farm injuries, fractures requiring vascular repair, or fractures that have been open for 8 h prior to treatment.

Type IIIA: Type III fracture with adequate periosteal coverage of the fracture bone despite the extensive soft-tissue laceration or damage.

Type IIIB: Type III fracture with extensive soft-tissue loss and periosteal stripping and bone damage. Usually associated with massive contamination. Will often need further soft-tissue coverage procedure (i.e. free or rotational flap).

Type IIIC: Type III fracture associated with an arterial injury requiring repair, irrespective of degree of soft-tissue injury.

According to some embodiments, the medical device of the invention is administered at a dose ranging from 1-40 grams per each single bone fracture site. According to certain embodiments, the medical device of the invention is administered at a dose ranging from 5-20 grams per one bone fracture site. It is to be understood that depending on the status of the fracture a higher or a lower dose can be used per one bone fracture at the discretion of the skilled in the art. Following the insertion, or implantation of the medical device of the invention into a bone fracture site, the coated bone void fillers release the drug into the bone void and the surrounding over a predetermined, prolonged, controlled period of time. The bone filler scaffold supports osteoconductive bone recovery, by re-absorbing and being replaced by bone during the healing process. In addition, its osteoconductive properties will enhance callus formation and bone healing, while the controlled, prolonged release of the anti-bacterial drug from the coating formulation successfully eradicates or prevents bone infection. The antibacterial activity of the released antibiotic is ancillary to the osteoconductive activity of the bone void fillers, and prevents its potential rejection or early absorption by bacteria related to local bone infection, and prevent the development of acute or chronic bone infections following contamination.

According to some embodiments, the method of the invention further comprises the step of hydrating the medical device prior to its application or implantation at the bone void site. According to some embodiments, the hydration of the medical device is achieved by mixing the medical device with an aqueous solution. According to some embodiments, the aqueous solution comprises saline. According to additional embodiments, the aqueous solution comprises an antibiotic agent, said antibiotic agent may be the same or different from the antibiotic agent within the matrix composition. According to further embodiments, the aqueous solution comprises an agent which induces or stimulates bone growth such as an osteoinductive factor, a growth factor or a combination thereof. According to additional embodiments, the aqueous solution comprises an antiseptic agent, an anti-inflammatory agent, a non-steroidal anti-inflammatory agent or a combination thereof.

Without wishing to be bound by any theory or mechanism of action, the aqueous solution mixed with the medical device, diffuses or permeates into the porous non coated bone filler. When the aqueous solution further comprises an active agent such as for example an antibiotic agent, the antibiotic agent permeated into the porous non coated bone filler is being released shortly after the application of the hydrated medical device to the bone void site, thereby obtaining an immediate or short-term release of the antibiotic agent. Thus, the device of the present invention enables short-term release as well as long-term or prolonged release of the antibiotic agent, hence providing an efficient means for antibacterial activity.

The methods of the invention may enable a complete reconstruction of the infected bone in only one operative session. Thus the methods disclosed herein may reduce significantly the time of bone healing and rehabilitation. According to some embodiments, the methods of the invention may further comprise at least some of the subsequently surgical steps of irrigation and debridement (I&D) and fracture stabilization that can follow the first surgical intervention by the application of the medical device of the invention at the fracture site. The methods of the present invention are advantageous over conventional bone grafting techniques for the treatment of open bone fractures as they enable immediate treatment post trauma in only one operation session, preferably, at the first and sole operation session, potentially without the need for multiple surgeries. It is to be understood, that depending on the status of the bone fracture, additional treatments comprising additional application of the medical device of the invention at the fracture site might be needed. For example, depending on the status of the bone fracture a second application of the medical device of the invention at the fracture site can be done at any time after the first treatment, at the decision of qualified physician.

The following examples are presented for illustrative purposes only and are to be construed as non-limitative to the scope of the invention.

EXAMPLES

Example 1

The Effect of Phosphatidylcholine Acyl Chain Length on the Release Rate of Doxycycline from Bone Particles Coated with the Matrix Composition According to Some Embodiments of the Invention The preparation of the matrix composition with either DMPC, DPPC or DSPC, which only differ by 2 and 4 carbons in the acyl chains (14, 16 and 18 carbons, respectively) significantly affected the release rate of Doxycycline during the prolonged, zero-order release phase (Table 1). However, the length of the acyl chains did not significantly alter the release profile of the fast release phase. There was a clear linear increase ($R^2=0.976$) in the release rate of the entrapped drug as a function of the reduced acyl chain length of the phospholipid used. There was more than 55% increase in duration of the release for DSPC (18:0) only vs. DMPC (14:0) only. In general, the preparation of the matrix composition with a mixture of these fully saturated phospholipids follows the same trend, but with some exceptions. In this regard, most notable is the strong effect of mixing DSPC with DPPC, where even a small portion of 24 mole % DSPC affected the release rate to the same extent as the 100% formulation of this lipid.

TABLE 1

The effect of di-saturated phosphatidylcholine acyl chain length in the matrix formulation on the release rate of DOX.

| PC composition | | | Release Rate |
|---|---|---|---|
| DMPC (mole %) | DPPC (mole %) | DSPC (mole %) | Median μg Doxy/day/mg BNP |
| 100% | | | 0.42 |
| 76% | 24% | | 0.36 |
| 52% | 48% | | 0.33 |
| 27% | 73% | | 0.35 |
| | 100% | | 0.32 |
| | 76% | 24% | 0.27 |
| | 52% | 48% | 0.28 |
| | 26% | 74% | 0.27 |
| | | 100% | 0.26 |

Bone particles coated with polymer-lipids-DOX formulations were prepared with defined single components di-saturated phosphatidylcholine (PC) and PCs mixtures, and the release of DOX was measured daily for 30 days. The median daily release rate during the zero-order kinetics phase was calculated and normalized to the amount of released drug from 1 mg of coated bone particles per day (μg DOX/day/mg coated bone particles).

The duration of the release of DOX from coated bone particles reflects the release rate measured during the linear phase (Table 2). The duration is dominated by the phospholipid that has the longer acyl chain, almost regardless of its relative content in the mixture. As with the release rate, this phenomenon is strongly evidenced for DSPC-DPPC mixtures, where any addition of DSPC shifted the release duration to be similar to the release rate with DSPC alone.

TABLE 2

The effect of di-saturated PC acyl chain length on the release duration of Doxycycline.

| PC composition | | | Release Duration |
|---|---|---|---|
| DMPC (mole %) | DPPC (mole %) | DSPC (mole %) | Release of 80% of the dose (Days post hydration) |
| 100% | | | 10.7 |
| 76% | 24% | | 14.6 |
| 52% | 48% | | 14.7 |
| 27% | 73% | | 15.5 |
| | 100% | | 17 |
| 76% | | 24% | 21 |
| 52% | | 48% | 22.5 |
| 26% | | 74% | 22.5 |
| | | 100% | 21.5 |

Example 2

The Effect of Saturated Vs. Unsaturated Phosphatidylcholine on Matrix Properties The matrix composition of the invention is saturated with lipids. The lipids are preferably saturated phosphatidylcholines and cholesterol. We have tested how the properties of the matrix composition (drug release properties, stability, ease of handling) are affected by changing the phosphatidylcholine from the saturated DPPC (16:0) to the non-saturated DOPC (18:1) without changing the amount and ratio of all other ingredients in the composition.

Results indicate that the overall release profile and release rate were not affected. However, TCP particles coated with a matrix composition comprising DOPC in contrast to DPPC were sticky, formed aggregates and were difficult to handle. In particular, homogenous mixture of coated and non coated particles was difficult to obtain.

Additionally, The TCP particles coated with a composition comprising DOPC were found to be unstable as indicated by the reduction in drug content during storage and by an observed change in color of bone particles coated with such composition. More particularly, while bone particles coated with a composition comprising DPPC maintained their yellowish color, the color of bone particles coated with a composition comprising DOPC was changed to brown within several days, possibly due to drug degradation.

Thus, DOPC is not suitable for use in the composition for stability concerns.

Example 3

The Effect of Cholesterol on Doxycycline Release from the Matrix Composition of the Invention The presence of cholesterol in the matrix composition significantly affected the release profile and release rate of Doxycycline during the prolonged, zero-order release phase. As can be seen in FIG. 1, upon reducing the amount of cholesterol in the formulation to 5% (w/w of the matrix composition) or lower the release of the antibiotic compound was not completed and was blocked after only 70% of the antibiotic compound was released. FIG. 1 also shows the importance of adding phosphatidylcholines having fatty acid moieties of 16 carbons to the matrix composition. When phosphatidylcholines were omitted from the composition, the antibiotic agent was release very rapidly, and full release was achieved within 10 days. Thus, the preparation of the matrix composition with at least DPPC, significantly affected the release rate of Doxycycline during the prolonged, zero-order release phase, enabling controlled release of the drug for at least 3-4 weeks.

Example 4

Figure 2:
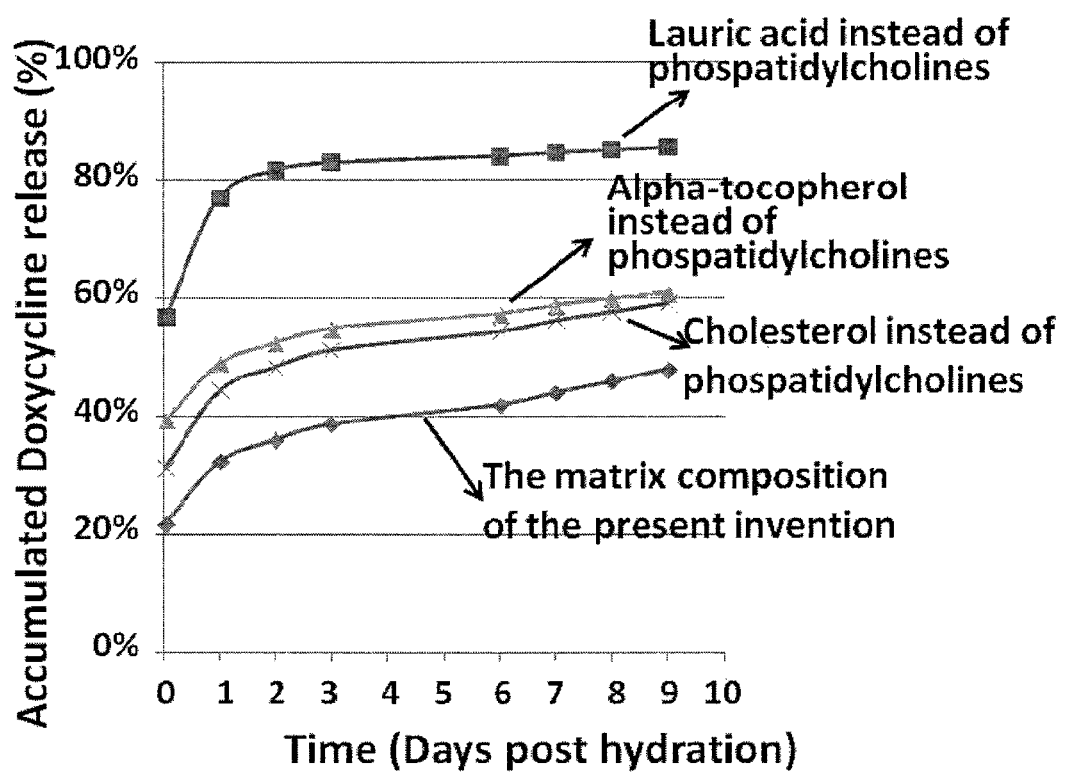
FIG. 2 shows the drug release profile of formulation in which phosphatidylcholines were replaced with alternative lipids.

The Effect of Different Lipids on Doxycycline Release from the Matrix Composition of the Invention The presence of phosphatidylcholines in the matrix composition of the invention is essential. Replacement of phosphatidylcholines with alternative lipids such as lauric acid, alpha tocopherol or cholesterol resulted with formulations characterized by higher initial burst release (>35%) (FIG. 2), which are not suitable for long term treatment.

Example 5

Performance Characteristics of the Medical Device of the Present Invention

The medical device studied in the following examples (unless indicated otherwise) comprises a 1:1 mixture of coated and non-coated TCP particles having an average size of 100-1000 μm, the coated TCP particles are coated with a matrix composition comprising 20% (w/w of the matrix composition) PLGA, 9,7% (w/w of the matrix comparison) of cholesterol, 45.23% (w/w of the matrix composition) of DPPC; 15.07% (w/w of the matrix composition) of DSPC and 10% (w/w of the matrix composition) of doxycycline hyclate.

Overall, the medical device studied in the following examples consists essentially of 93.50% (w/w) β-TCP particles having an average size of 100-1000 μm; 1.3% (w/w) PLGA; 0.63% (w/w) of cholesterol; 2.94% (w/w) of DPPC; 0.98% (w/w) of DSPC and 0.65 (w/w) of doxycycline hyclate, unless otherwise indicated.

Process for the Preparation of the Medical Device of the Invention

Preparation of Solutions:

SS1—PLGA was dissolved in EA to a concentration of 300 mg/ml.

SS2—Cholesterol (CH) was dissolved in EA to a concentration of 30 mg/ml.

Solution A—One volume of SS1 was mixed with five volumes of SS2 (PLGA 50 mg/ml; CH 25 mg/ml). The solution was kept at room temperature for 10 minutes.

EA:MeOH—EA and MeOH were mixed together in a ratio of 50:50 (SS2.1).

SS3—Doxycycline was dissolved in SS2.1 to a concentration of 50 mg/ml.

Solution B—DPPC and DSPC were dissolved with three volumes of SS3 and one volume of EA (DPPC+DSPC 225 mg/ml; Doxycycline 37.5 mg/ml).

Solution AB—Two volumes of solution B were mixed with three volumes of solution A (DPPC+DSPC 60 mg/ml; PLGA 20 mg/ml; Doxycycline 10 mg/ml; CH 10 mg/ml).

Coating Step:

1 gr of cleaned β-TCP particles was placed in a 20 ml vial.

1000 μl of solution AB were added to the vial containing the β-TCP and the solvents were left for evaporation on a heating mantle set to 45° C. till dryness (75 minutes).

The sample was put in vacuum (1 Pa.) overnight to ensure complete solvent evaporation.

It is to be emphasized that the mixing of coated and non coated bone fillers facilitates bone growth immediately after implantation of the medical device of the invention at a location where bone growth is desired. Upon gradual surface degradation of the matrix composition, there is no difference between the ability to support bone growth of the non-coated bone fillers and the bone fillers which surface was exposed after gradual surface degradation of the matrix.

Stability of Doxycycline in the Matrix Compositions of the Present Invention

Figure 3:
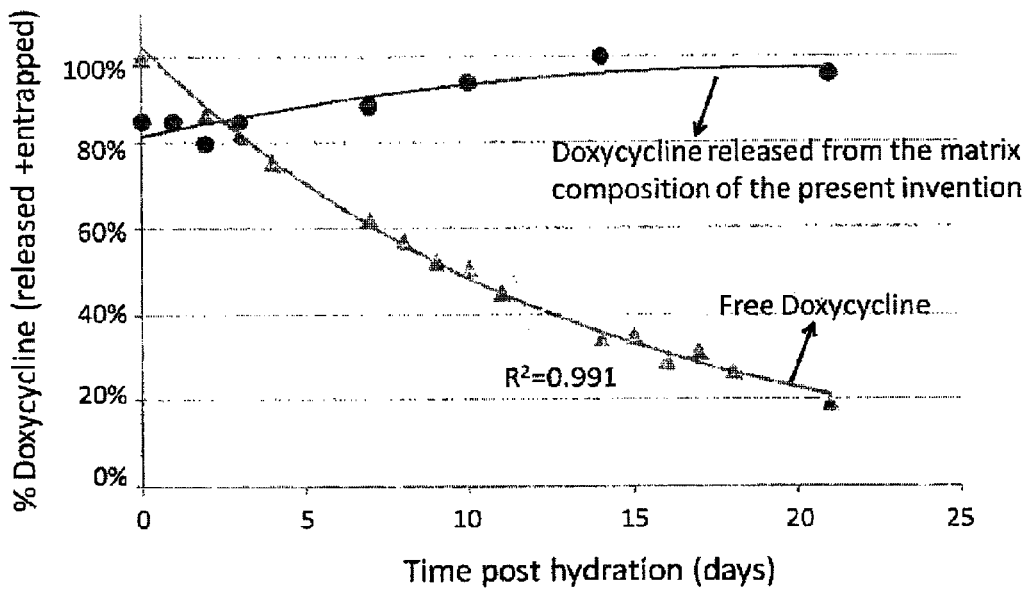
FIG. 3 shows the stability of doxycycline entrapped within the matrix composition of the present invention versus free doxycycline.

Doxycycline is known to degenerate under hydrating conditions. The matrix composition of the present invention can protect Doxycycline from this degradation. The stability of the entrapped Doxycycline during the hydration of the matrix composition (in FBS solution at 37° C.) was tested. At each time point two parameters were tested: 1) Doxycycline molecules released from the medical device of the invention and 2) Doxycycline molecules reservoir in the medical device of the invention. The latter was extracted from the formulation using methylene chloride. The sum of the two Doxycycline quantities represents the overall quantity of Doxycycline in the product at each time point. Free Doxycycline, incubated under the same conditions, was used as control. Results are plotted in FIG. 3.

While free Doxycycline is degraded exponentially, as expected ($R^2>0.99$), leading to a sharp reduction in the concentration of Doxycycline, the sum of the released and the entrapped drug in the matrix composition remains constant and well above 90% of the initial dose. After hydration for 21 days the overall doxycycline molecule (released+reservoir) exceeded 95% of the initial dose, whereas of the free Doxycycline only 20% remained intact.

Figure 4:
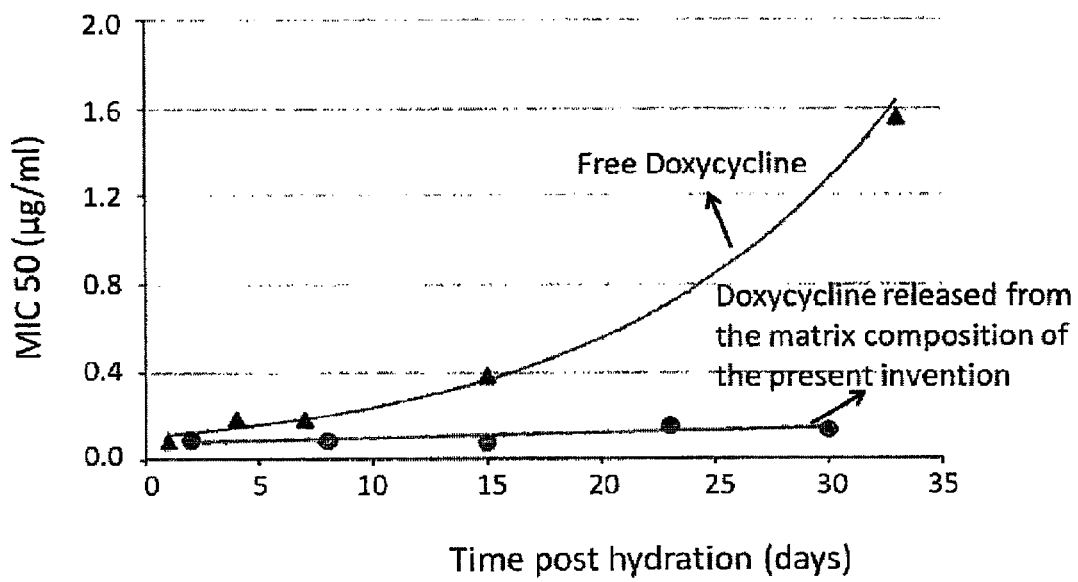
FIG. 4 shows the antimicrobial activities of doxycycline released from bone particles coated with the matrix composition of the invention vs. the activity of free Doxy incubated in hydrous solution.

The Antimicrobial Activities of Doxycycline Released from the Matrix Composition of the Present Invention The antibacterial activity against *Staphylococcus aureus* (ATCC 25923), of Doxycycline that was released from bone particles coated with the matrix composition of the invention was followed for a period of 30 days following its hydration (FIG. 4). The MIC (Minimal Inhibitory Concentration) for Doxycycline that was released from the matrix composition at different time points was calculated to be ~1 µg/ml, and MIC 50 (the concentration that inhibits 50% growth) was ~0.1 µg/ml, values that were similar to the control free Doxycycline. However, as expected from its low stability post hydration, the activity of the hydrated free Doxycycline was lost gradually, whereas Doxycycline that was released from the medical device of the present invention preserved its potency for the whole test period (FIG. 4).

In-Vitro Studies

Taking advantage of the large surface area of the TCP granules which exceed 50 $m^2/g$, the fine coating with the matrix composition of the present invention can accumulate into a significant overall mass of about 5%-15% of the bone filler with no significant change in its overall dimension. The overall mass of Doxycycline antibiotics is about 0.65% of the overall mass of the medical device tested (see above). This is much lower concentration than other local delivery systems used for the treatment of bone infections, such as the non-biodegradable PMMA beads (5%-10%) or the biodegradable OSTEOSET T® (4%).

Release Profile of Doxycycline from the Medical Device of the Present Invention

The very fine antibacterial layer coating, up to 20 µm, does not significantly alter the original shape and size of the TCP granules. It does not change the properties of the cement, or the way surgeons use it as a bone filler. The coating formulation components are all completely biocompatible and biodegradable. Upon hydration in the body, the formulation is gradually disintegrated from the outside, layer by layer. The degradation allows the entrapped antibiotic in the outer layer to be released constantly into its surrounding.

Drugs encapsulated in drug delivery systems composed of either polymers or lipids are released in a logarithmic regimen. In the medical device of the invention, the doxycycline compound is encapsulated in a formulation composed of both polymers and lipids, which not only attenuate the release of the drug, but also alter the release kinetics. The release rate of Doxycycline from the coating of the combination of polymer and lipids provides a prolonged release rate with zero-order kinetics for most of the entrapped dose ($P>0.97$).

Figure 5:
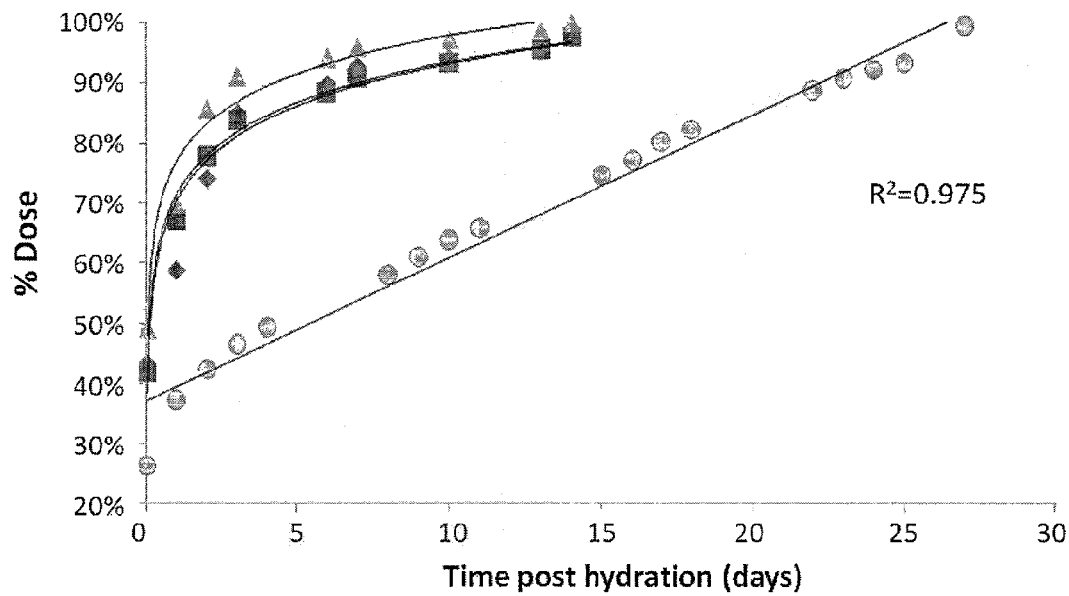
FIG. 5 shows the accumulated release profile of doxycycline from hydrated bone particles coated with the matrix composition of the invention vs. the release profile of free doxycycline (triangles); compositions composed of phospholipids and doxycycline (diamonds) and compositions composed of PLGA and doxycycline (squares).

The in-vitro release of Doxycycline from granules of the medical device of the invention is initiated by the hydration of the granules at body temperature or thereabout. Typically about ~20-30% of the drug content is released into the supernatant within the first day following the hydration, when most of the initial release occurs after the first hour (FIG. 5). Following the initial release, about 70% of the dose is released in zero-order kinetics at the rate of about 3% of the overall dose. After ~4 weeks the release rate is significantly decreased and the release of Doxycycline is practically stopped. By plotting the accumulated released of a drug over time a linear "zero order" release kinetics ($R^2=0.98$) of 60%-70% of the entrapped dose is observed, starting from day 2 until day 26 (FIG. 5, circles). In contrast, the release profiles of Doxycycline from the control groups: (a) TCP granules that were treated by the same process as with the medical device of the invention but only with the drug itself, (b) the PLGA polymer that was formulated with the drug and (c) the drug that was formulated with phospholipids, were all significantly faster than that of the group with coated particles of the invention. Furthermore, the release kinetics of the drug from the TCP granules of group (a) were characterized by first order exponentially accumulated logarithmic drug release that differs from the release profiles of Doxycycline from the coated particles of the invention (FIG. 5). The drug release profile was similar in all the three control formulations, and the initial Doxycycline release was rapid, accumulating to ~40% after 1 hour and >80% during the first 4 days post hydration.

Example 5

Effectiveness of the Medical Device According to Certain Embodiments of the Invention in Infected Rabbits' Tibia Model The medical device according to certain embodiments of the invention has been tested in vivo in infected rabbits' tibia model. The medical device has demonstrated its high effectiveness both in acute and in chronic infections, as well as proving to be significantly advantageous over the non-formulated free drug. The greater effectiveness of the medical device of the invention in bone healing derives from its linear sustained long term release of the product (doxycycline) over a period of 4 weeks and its osteoconductive effect as a bone filler.

Example 6

Effectiveness of the Medical Device According to Certain Embodiments of the Invention in the Treatment of Open Contaminated/Infected Fractures The study aims to demonstrate the effectiveness of the medical device according to certain embodiments of the invention as an osteoconductive agent (for enhancing callus formation and bone healing) and to demonstrate the ancillary activity of the medical device of the invention by the reduction or eradication of local bone infection in contaminated or infected open fractures demonstrated in bacterial cultures.

The study aims to demonstrate the safety of the medical device of the invention in the treatment of open fractures as assessed by: Reporting and recording adverse events and Laboratory variables: Blood hematology, serum chemistries and urinalysis.

Clinical Study Design

Study Design

The device according to the present protocol provides bone filler and a sustained antibiotic release platform. The bone filler is resorbed and replaced by bone during the healing process and the antibiotic eradicates or reduces local bone infection and allows for successful bone healing.

Study involves about 16 subjects, hospitalized with long bone fractures (Gustilo stage II, IIIa or IIIb), will be included.

Inclusion Criteria

Men and women of age 18-70 years old

Open long bone fractures

Severity of fractures: Gustilo grade II, IIIa and IIIb

Patients with Gustilo type II, IIIa, IIIb and IIIc long bone open fractures were enrolled up to 6 days post trauma. In cases where patients have already been treated with systemic antibiotics post trauma and prior to implementation of the medical device according to the methods of the invention, longer duration post trauma is possible. Patients with Gustilo type II, IIIa and IIIb long open fractures who are multiply injured may be enrolled into the clinical study as long as they are hemodynamically and physiologically stable. As used herein "a multiple-injured patient" is a patient suffering from at least two injuries, each injury may be requiring a separate and independent hospitalization.

Any additional antibiotics, except for those listed as standard of care (SOC) of the Hospital, are not allowed per clinical trial protocol.

Patients received IV antibiotics, followed by Oral antibiotics (as needed), according to SOC of the Hospital.

Doxycycline IV/PO administration was not allowed in this protocol.

Long term steroids use and/or Immunosuppressive agents were prohibited during the course of the trial.

Study Period

The maximum duration of this study was 12 weeks for a given patient. Additional follow-up post study termination were done at the discretion of the attending physician, according to his medical practice and included at least one follow up study 6 months post study. Exemplary study task flow charts are presented in FIGS. 1A and 1B. According to some embodiments, the pharmacokinetics (PK) of blood doxycycline may be excluded from the study task flow chart as described in FIG. 1B.

Screening Visit—Visit 1, Day −1 at the Emergency Room (ER)

The screening visit included documentation of fracture status (photos of the wound taken); Physical examination; Bacteriological tests (swabs from fractured bone and fascia surrounding soft tissue); Wound is washed with 500 ml sterile saline; Wound assessment; Sterile dressing—to be opened only at debridement; Systemic antibiotic initiation—standard of care (SOC); X-ray (anteroposterior & lateral); Ancillary procedures as per local SOC, e.g., blood transfusion, anesthesia evaluation.

Visit 2: Day 0/Baseline at the Operating Room (OR)

Visit 2 included: Fracture status (+ photos); Irrigation and debridement procedure (I&D); Fracture stabilization (Ex-Fix or cast); Treatment with the medical device of the present invention—The medical device is applied as bone void filler into the fracture site; Sterile dressing; X-ray (AP+LAT) and Wound assessment+Systemic antibiotic (if needed).

Visit 3: Day 1 at the Hospital:

Visit 3 included wound assessment+systemic antibiotics (if needed).

Visit 4 at the OR in the Hospital— Between Days 2-6 (at the Discretion of the Attending Physician)

Visit 4 included Fracture status (+photos); bacteriological tests (swabs from fractured bone and fascia surrounding soft tissue), (before any I&D and/or wound closure); Wound assessment+systemic antibiotic (if needed); Irrigation and debridement; Fracture stabilization (Ex-Fix or cast); additional treatment with the medical device of the invention (only if needed); wound closure/dressing and sterile dressing (if needed)

Visits 5, 6, 7 on Days 7, 14 and 21 at the Hospital

Visits 5-7 included Wound assessment+systemic antibiotics if needed.

Visit 8—4 Weeks after Initial Treatment at the Hospital

Visit 8 included assessment of the fracture status (+photos); Physical examination; bacteriological tests (swabs from fractured bone and fascia surrounding soft tissue) (if needed—At drain removal/Once a week if drainage from the wound continues); X-ray (AP+LAT) and wound assessment and treatment at PI discretion: Wound criteria for infection: positive growth bacteriology, and/or presence of drainage/purulence even if the bacteriology result is negative. In case of continuous secretion, systemic antibiotic will be administered at the discretion of the attending physician Visit 9—Visit 9, 8 weeks after Initial Treatment at the Hospital Visit 9 included assessment of the fracture status; Physical examination; Bacteriological tests (swabs from fractured bone and fascia surrounding soft tissue) (if needed—At drain removal/Once a week if drainage from the wound continues); X-ray (AP+LAT); Wound assessment and treatment (systemic antibiotics if needed) at PI discretion. In case of continuous secretion, treatment was decided by the attending physician (as per Visit 8).

Study Follow Ups—Visits 10, 11, 12, 13 (12, 16, 20 and 24 Weeks Respectively after Initial Treatment at the Hospital Study follow up visits included assessment of the fracture status; Wound assessment; Bacteriological tests (only if wound is open/secretes and/or pin wound is open/secretes); X-ray ((AP+LAT) and Oblique 45° angle (as needed according to site medical practice))

During all visits including study follow ups visits blood test (hematology and blood chemistry) as well as vital signs (blood pressure, HR and body temperature) were measured. In all visits adverse events and concomitant medications were recorded.

Composition of Medical Device

The medical device according to some embodiments of the invention comprises:

TCP—510(k) Number K042340 CE Mark: CE 0459, Cholesterol—DMF 25382, PLGA—Purasorb DMF 21817, Phospholipids—DMF 7349.

The coated bone void fillers according to the invention are produced in compliance with ISO-9001 and ISO-13485 guidelines, done under aseptic conditions, and the product complies with all limitations stated by the USP for implanted medical devices.

According to certain typical embodiments, the concentration of the antimicrobial agent (e.g. Doxycycline Hyclate) (DMF 13636) used in the medical device according to the invention is 0.65% which is equivalent to 65 mg in each 10 g (1 vial) of the total weight of the medical device.

Method of Treatment

The coated bone void filler according to the invention is a biocompatible, biodegradable, disposable device, provided pre-loaded and pre-sterilized for single patient use, packaged in a sterile, amber vial of 10 g ready for use product. Each vial contained 10 grams of medical device, including 0.5-1 mm TCP granules half of which were coated with the matrix composition of the invention. Every 10 grams of medical device contained a total of 65 mg doxycycline.

According to some embodiments, the amount of medical device to be implanted at a bone fracture site or at any other bone void site depends on the size of the bone void to be filled by the bone filler. According to some embodiments, the maximum recommended dose of the medical device to be implanted at the bone fracture site for an adult is 2 vials (20 g) in one use and a total of 4 vials (40 g) for this particular study. In very rare cases, depending on the status of the fracture a higher dose can be used at the discretion of the skilled in the art. Due to the very low dose of Doxycycline applied in the matrix composition of the invention and its local use, no safety issues are anticipated.

According to some currently preferred embodiments, the medical device of the invention will be administered at the bone void fracture site on Visit 2 (operating room). An additional 10-20 g of the medical device per implantation may be used, at the discretion of the orthopedic surgeon, based on the size of the wound/void. A total of 20 g (two vials) may be used at any time after Irrigation and debridement procedure in the operating room.

Following bacteriology test and Irrigation and debridement procedure, approximately 3 days after Visit 2 (Visit 4, day 2-6 at the operating room), the attending physician may decide to re-administer treatment with coated bone particles.

The Surgical Procedure:

According to some embodiments, the surgical procedure may be any surgical procedure known in the art for the treatment of bone fractures. Proper surgical procedures and techniques are the responsibility of the professional physician/surgeon.

Precautions:

As with any surgical procedure, care should be exercised in treating individuals with pre-existing conditions that may affect the success of the surgical procedure. These include individuals with bleeding disorders, use of long term steroids (add to the protocol), immunosuppressive therapy etc.

There are no safety issues associated with implantation of the matrix composition of the invention nor with bone filler particles coated with the matrix composition. All safety parameters taken following implantation—such as: blood count, erythrocyte sedimentation rate (ESR), bacterial culture of the void, Anteroposterior & lateral X-ray, wound assessment, and adverse events—are related to the traumatically bone fractures that is associated with potential infection.

Adverse Events may include: sensitivity to the tetracycline family of antibiotics; wound complications, including hematoma, site drainage, and bone infection; complications of any surgery; transient hypercalcemia. It is to be emphasized that in case of severe hypersensitivity to Doxycycline, the treatment shall be stopped immediately.

The medical device was kept refrigerated at all times before use and extended exposure to strong light or heat was avoided.

Before implantation the medical device was poured into an open sterile cup and wetted with 4 ml if saline (not distilled water) per 10 grams of medical device. Excessive wetting should be avoided.

After hydration the medical device is implanted at the fracture site. The bone void at the fracture site should be filled completely.

Storage Conditions

Bone filler coated with the matrix composition of the invention was stored at 2-8° C. (For a period shorter than 24 hours, the coated bone filler may be stored at room temperature (between 18 and 25° C.)), and protected from light and humidity.

Assessment of Methods

Efficacy Assessment Methods

The effectiveness of the medical device of the invention was assessed at 4 and 8 weeks post initial treatment by:
1. % of negative bacterial cultures
2. % of soft tissue wound closure (physical dimensions)
3. % of callus formation as reflected by X-ray on at least 2 projections: AP+LAT at 4, 8 and 12 weeks following medical device administration Clinical Trial Results of 16 Patients with Gustilo IIIA and IIIB Open Long Bone Fractures Treated with the Medical Device of the Invention:

β-tricalcium phosphate bone void filler (TCP) coated with formulated doxycycline according to certain embodiments of the invention was implanted during the first surgical intervention concomitantly with standard of care (SOC). Patients went through periodic routine hematology, biochemistry, urinalysis, bacteriology and radiologic follow up.

Results: 14 males and 2 females (mean age 37±9), 11 subjects with Gustilo IIIA and 5 with IIIB were enrolled (Table 1).

TABLE 3

Patients profile

| | | |
|---|---|---|
| Gender | 14 Males | 2 Females |
| Age | 21-55 yrs | Ave. 31.1 yrs |
| Laterality | 11 Left leg | 5 Right leg |
| Gustilo grade | 11 IIIA | 5 IIIB |
| Cause of Injury | Motorbike/driver 6 | Moterbike/passenger 2 |
| | Pedestrian - 4 | Blunt - 2 |
| | Crush - 1 | Fall - 1 |
| Enrolment time post trauma (hr.) | 0.5-132 | Aver. 20.8 |

Figure 6:
FIG. 6 shows the results of a treatment of 49 years old male with an open tibia and fibula fracture graded Gustilo IIIA with an open wound dimension of 2×2 cm, enrolled 1.5 hours post trauma. X-ray images of the open tibia fracture site post trauma.
Figure 7A:
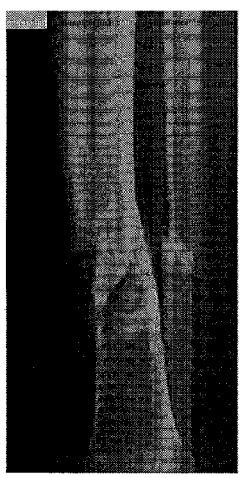
FIG. 7 shows X-ray images of an open tibia (including fibula) fracture graded Gustilo IIIA with an open wound dimension of 2×2 cm, 49 years old male enrolled 1.5 hours post trauma treated by methods according to some embodiments of the invention. A) Open tibia fracture post trauma; B) fracture at day 0, immediately after medical device implantation; C) 4 weeks post implantation; D) 8 weeks post implantation. The X-ray images show excellent wound recovery at 8 weeks after the initial, sole, surgical intervention.
Figure 7B:
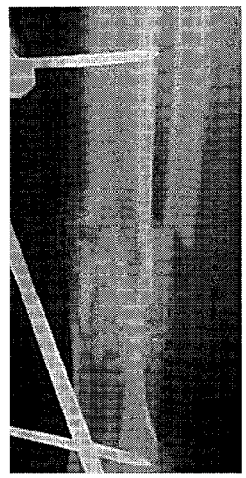
Figure 7C:
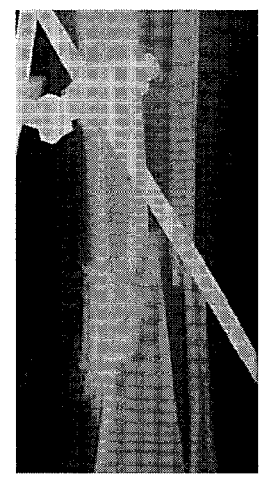
Figure 7D:
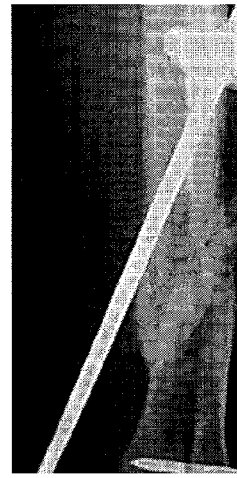
Figures 8A, 8B:
FIG. 8 shows the results of a treatment of a patient with a tibia fracture Gustilo IIIB, enrolled 4.5 hours post trauma. A, B) X-ray images of the tibia fracture site post trauma; C)) X-Ray of the fracture site post implantation vs. 12 weeks after implantation: initial callus formation is seen only where the coated bone filler was implanted into the bone void.
Figure 8C:
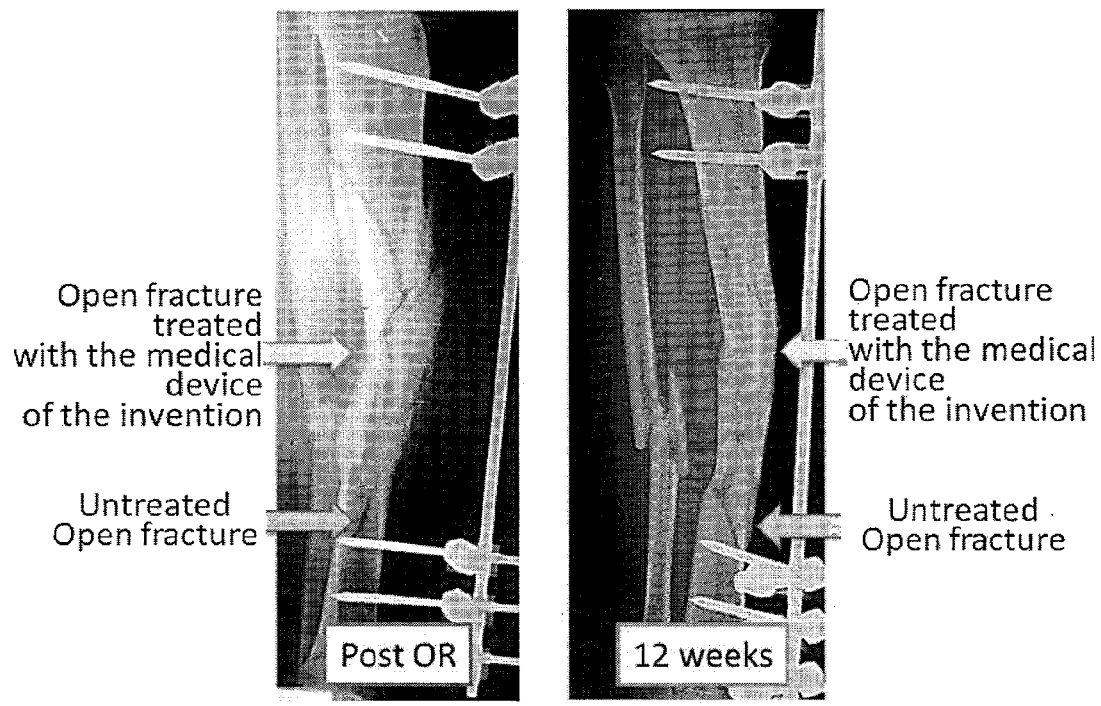
Figures 9A, 9B, 9C, 9D:
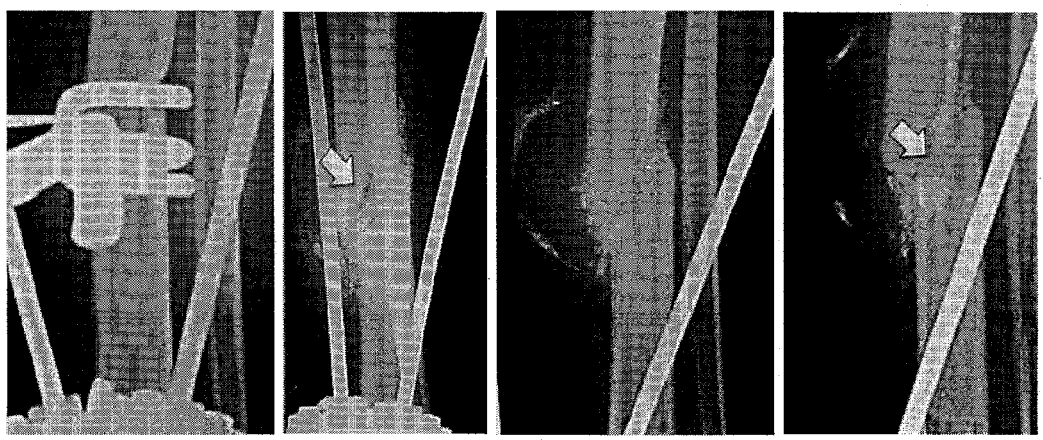
FIG. 9 shows X-ray images of a tibia fracture site of a patient enrolled 10 hours post trauma. A) tibia fracture post trauma immediately after medical device implantation; B) fracture site 4 weeks post implantation, the arrow points the fracture site; C) fracture site 8 weeks post implantation; D) fracture site 12 weeks post implantation.
Figure 10A:
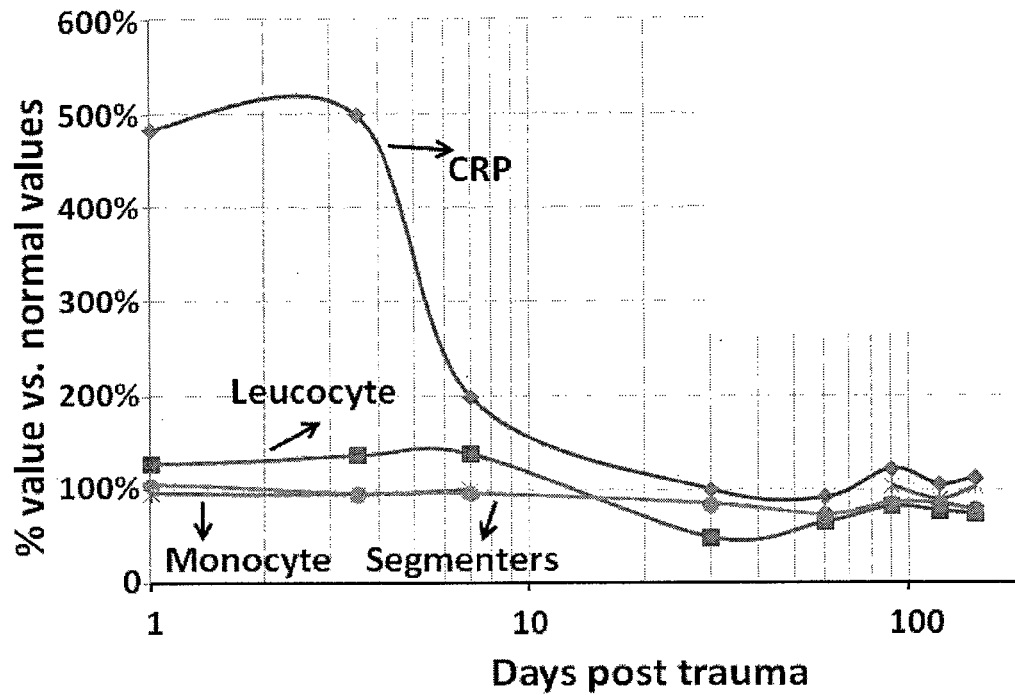
FIG. 10 shows A) the average CRP levels of 16 patients with contaminated open bone fractures types IIIA and IIIB treated with the medical device of the invention; B) CRP levels in patients with and without postoperative surgical-site infection (the figure was adapted from a publication by HO Ayo, SA Orthopaedic J., 2010, P. 24-29).
Figure 10B:
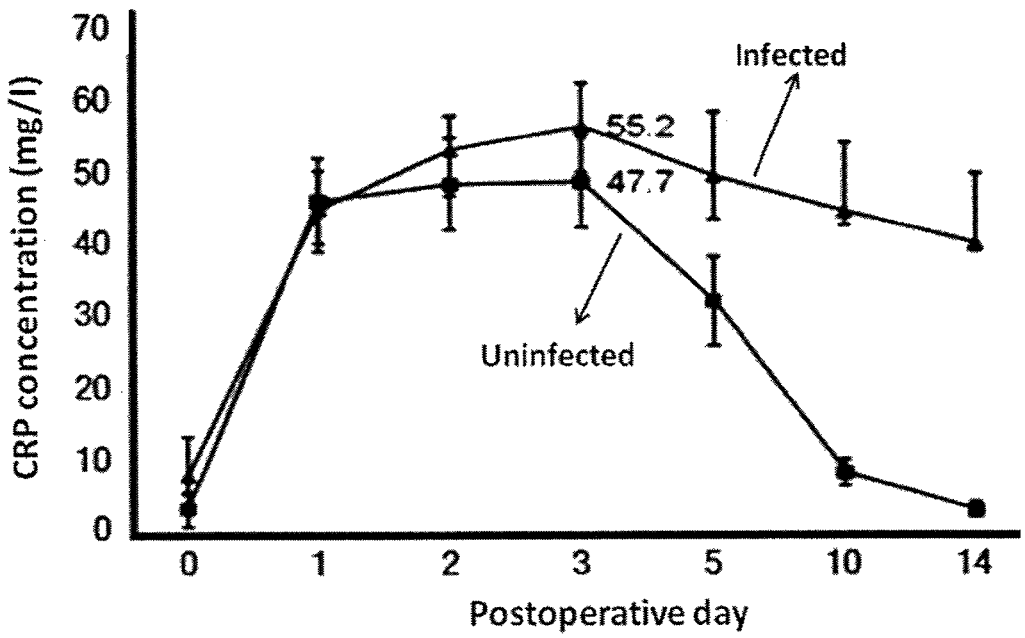

The target open fracture in all patients treated was tibia Enrolment time since trauma was above 8 hours for 7/16 patients, one of the treated subject was enrolled 132 hours post trauma. The preliminary results at 12 weeks have shown that no infection was reported at the target fracture implanted by β-TCP bone void filler coated with formulated doxycycline (only one deep infection reported at the fibula fracture where no β-TCP bone void filler coated with formulated doxycycline was implanted). Only one incision and drainage (I&D) needed and performed in the target fracture. Subsequent surgical procedures were done only to the soft tissues (5 skin implantation, 3 soleus flaps). Early callus formation was observed at 6-12 weeks post implantation. FIG. 6 and FIG. 7 (A-D) show the results of a treatment of 49 years old male with an open tibia (including fibula) fracture graded Gustilo IIIA with an open wound dimension of 2×2 cm, enrolled 1.5 hours post trauma. FIG. 8 (A-C) shows the results of a treatment of a patient with a tibia fracture Gustilo IIIB, enrolled 4.5 hours post trauma. FIG. 9 (A-D) shows the bone recovery of a patient with a tibia fracture enrolled 10 hours post trauma.

No adverse events associated with the β-TCP bone void filler coated with formulated doxycycline according to the invention as well as no serious adverse events were reported (Table 2).

TABLE 4

Experimental results

| Surgical incisions/ Wound closure | 8 primary wound closure after first target fracture incision and drainage (I&D) | Soft tissue wound: 5 required skin grafts 3 required soleus flaps | All surgical incisions healed |
|---|---|---|---|
| Infection reported | None in target bone fracture | 7 Superficial nosocomial infections - soft tissue wounds | 1 deep infection in Fibula, (was not treated with the medical device of the present invention) |
| Callus formation | in all target fractures implanted by the medical device of the present invention | Early callus formation | 8-12 weeks |

Safety results: Adverse events reported by patients treated with the medical device of the present invention were mild to moderate. No serious adverse events or death were reported.

The dramatic infection reduction of bone fracture sites upon treatment with the medical device of the present invention is demonstrated in FIG. 6A. FIG. 6B taken from a publication by HO Ayo (SA Orthopaedic J, 2010, P. 24-29) demonstrated the CRP levels in patients with and without postoperative surgical-site infection. C-reactive protein (CRP) is a protein found in the blood, the levels of which rise in response to inflammation.

As can be seen in FIG. 6B, the CRP levels in patients without postoperative surgical-site infection increases after the surgical procedure, yet levels down back to normal values between 10-14 days post operation. CRP levels in patients suffering from infection remain very high even after 2 weeks post operation.

FIG. 6A shows the average measured levels of C-reactive protein (CRP) in the blood of 16 patients treated with the medical device of the present invention.

As can be seen in FIG. 6A, 10-12 days after being treated with the medical device of the invention the levels of CRP have been reduced to normal healthy levels indicating that no infection was developed at the target fracture treated. Normal CRP levels were observed even more than 100 days post treatment.

Conclusions: A strong clinical signal of both osteoinductive and anti-infective effects of β-TCP bone void filler coated with formulated doxycycline according to some embodiments of the invention (mixed with non-coated β-TCP) was demonstrated in very severe open long bone fractures patients. Using the compositions and methods of the present invention no infection was observed in any of the treated patients even 6 months post treatment. The fractures were fully united in over 75%, after being treated with the medical device of the invention in a single operative session, without developing any infection at the target fracture.

The TCP particles coated with the matrix composition of the invention promote the bone healing process while preventing infection in a single treatment.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A medical device comprising coated and non-coated bone filler particles at a ratio of between about 1:3-10:1, wherein the coated bone filler particles comprise between about 80-90% (w/w) of bone filler and between about 10-20% (w/w) of a matrix composition which comprises: (a) 15-25% (w/w) PLGA; (b) 5-15% (w/w) of cholesterol; (c) 50-70% (w/w) of a mixture of DPPC and DSPC, wherein the ratio of DPPC to DSPC is between 5:1 and 2:1 and (d) 7-12% (w/w) of doxycycline or doxycycline hyclate.

2. The medical device of claim 1, wherein the bone filler is selected from the group consisting of allogeneic bone filler, xenogeneic bone filler, synthetic bone filler and a combination thereof.

3. The medical device of claim 2, wherein the bone filler is synthetic bone filler.

4. The medical device of claim 3, wherein the synthetic bone filler is Tri-Calcium Phosphate (β-TCP).

5. The medical device of claim 4, wherein the β-TCP has an average particle size of up to 1 mm.

6. The medical device of claim 1, wherein the weight ratio between the coated bone particles and non-coated bone particles is about 1:1.

7. The medical device of claim 1, wherein the doxycycline or doxycycline hyclate is present at 0.4-2% (w/w) of the total weight of the medical device.

8. The medical device of claim 4 comprising (a) 90-95% (w/w) of β-TCP; (b) 1.0-2.0% (w/w) PLGA; (c) 0.4-0.8% (w/w) cholesterol; (d) 2.0-4.0% (w/w) of DPPC; (e) 0.7-1.3% (w/w) of DSPC; (f) 0.4-2% (w/w) of doxycycline or doxycycline hyclate.

9. The medical device of claim 1 for implantation at a location at which bone growth is desired.

10. A biocompatible matrix composition, comprising: (a) 15-25% (w/w) PLGA; (b) 5-15% (w/w) of cholesterol; (c) 50-70% (w/w) of a mixture of DPPC and DSPC, wherein the ratio of DPPC to DSPC is between 5:1 and 2:1 and (d) 7-12% (w/w) of doxycycline or doxycycline hyclate.

11. A method for treating an open bone fracture in a patient comprising implanting at the fracture site a medical device comprising coated and non-coated bone filler particles at a ratio of between about 1:3-10:1, wherein the coated bone filler particles comprise between about 80-90% (w/w) of bone filler and between about 10-20% (w/w) of a matrix composition which comprises: (a) 15-25% (w/w) PLGA; (b) 5-15% (w/w) cholesterol; (c) 50-70% (w/w) of a mixture of DPPC and DSPC, wherein the ratio of DPPC to DSPC is between 5:1 and 2:1; and (d) 7-12% (w/w) of doxycycline or doxycycline hyclate.

12. The method of claim 11, wherein the medical device provides local prolonged release of doxycycline or doxycycline hyclate at the fracture site.

13. The method of claim 11, wherein the open bone fracture is an open long bone fracture.

14. The method of claim 13, wherein the open long bone fractures are selected from bone fractures classified Gustillo grade II, IIIa, IIIb and IIIc.

15. The method of claim 14, wherein the open long bone fractures are selected from bone fractures classified Gustillo grade Ma and IIIb.

16. The method of claim 11, wherein the coated bone void filler is selected from the group consisting of allogeneic, xenogeneic, synthetic bone void fillers or any combination thereof.

17. The method of claim 16, wherein the bone filler is a synthetic bone filler.

18. The method of claim 17, wherein the synthetic bone filler is Tri-Calcium Phosphate ($\beta$-TCP).

19. The method of claim 11, wherein the medical device is applied at a dose of 50 grams or lower per bone fracture site.

20. The method of claim 11, wherein implanting is performed during the first surgical intervention at the bone fracture after the occurrence of injury.

21. The method of claim 20, wherein implanting is performed during the first surgical intervention at the bone fracture site after an irrigation and debridement (I&D) procedure.

\* \* \* \* \*